United States Patent [19]

McLachlan et al.

[11] Patent Number: 4,707,134
[45] Date of Patent: Nov. 17, 1987

[54] FIBER OPTIC PROBE

[75] Inventors: Richard D. McLachlan; Leslie D. Rothman, both of Midland, Mich.

[73] Assignee: The Dow Chemical Company, Midland, Mich.

[21] Appl. No.: 678,115

[22] Filed: Dec. 4, 1984

[51] Int. Cl.$^4$ .............................................. G01N 21/49
[52] U.S. Cl. ................................. 356/342; 250/564; 250/574; 250/227
[58] Field of Search ............... 356/342, 446; 250/564, 250/574, 227

[56] References Cited

U.S. PATENT DOCUMENTS 3,068,739 12/1962 Hicks, Jr. et al. .............. 356/342 X
3,781,555 12/1973 Keefe ................................ 250/227
4,573,761 3/1986 McLachlan et al.

FOREIGN PATENT DOCUMENTS 0017007 10/1980 European Pat. Off. ............ 356/342
2840867 4/1980 Fed. Rep. of Germany ...... 356/342
8203460 10/1982 PCT Int'l Appl.

OTHER PUBLICATIONS

Papa et al., "Turbidity Monitoring by Fiber Optics Instrumentation" *Applied Optics*, vol. 22, No. 3, pp. 375-376, 2/83.

*Primary Examiner*—Davis L. Willis
*Assistant Examiner*—Matthew W. Koren

[57] ABSTRACT

A fiber optic probe having a sealed, cylindrical housing closed at one end by a transparent window and at the opposite end by a wall through which a plurality of optical fibers extend toward the window. Adjacent the window the fibers are radially and circumferentially spaced about the axis of the housing and converge along lines which intersect one another at a common point on the housing axis that is adjacent or beyond the outer surface of the window. At least one of the fibers transmits light from a source through the window to illuminate a zone of a fluid sample, whereby particles present in such zone scatter light therefrom to the remaining fibers for transmission through the probe housing to light detecting and measuring apparatus.

24 Claims, 6 Drawing Figures

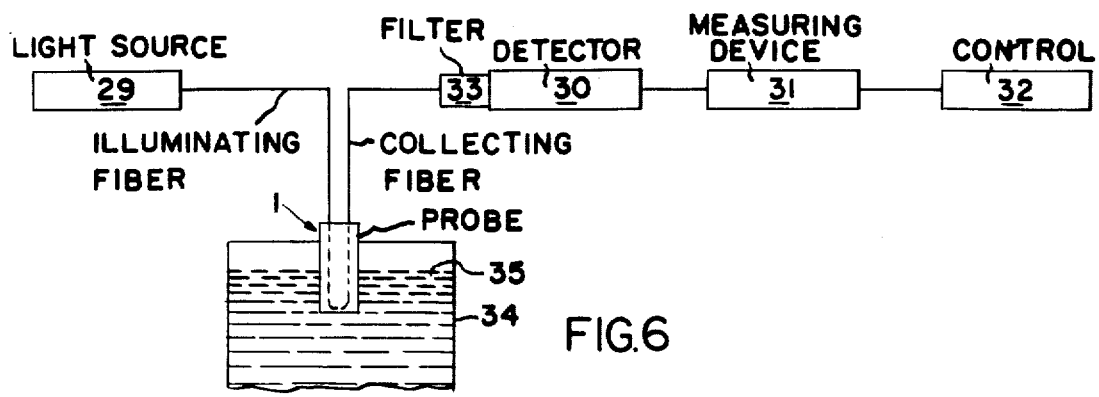
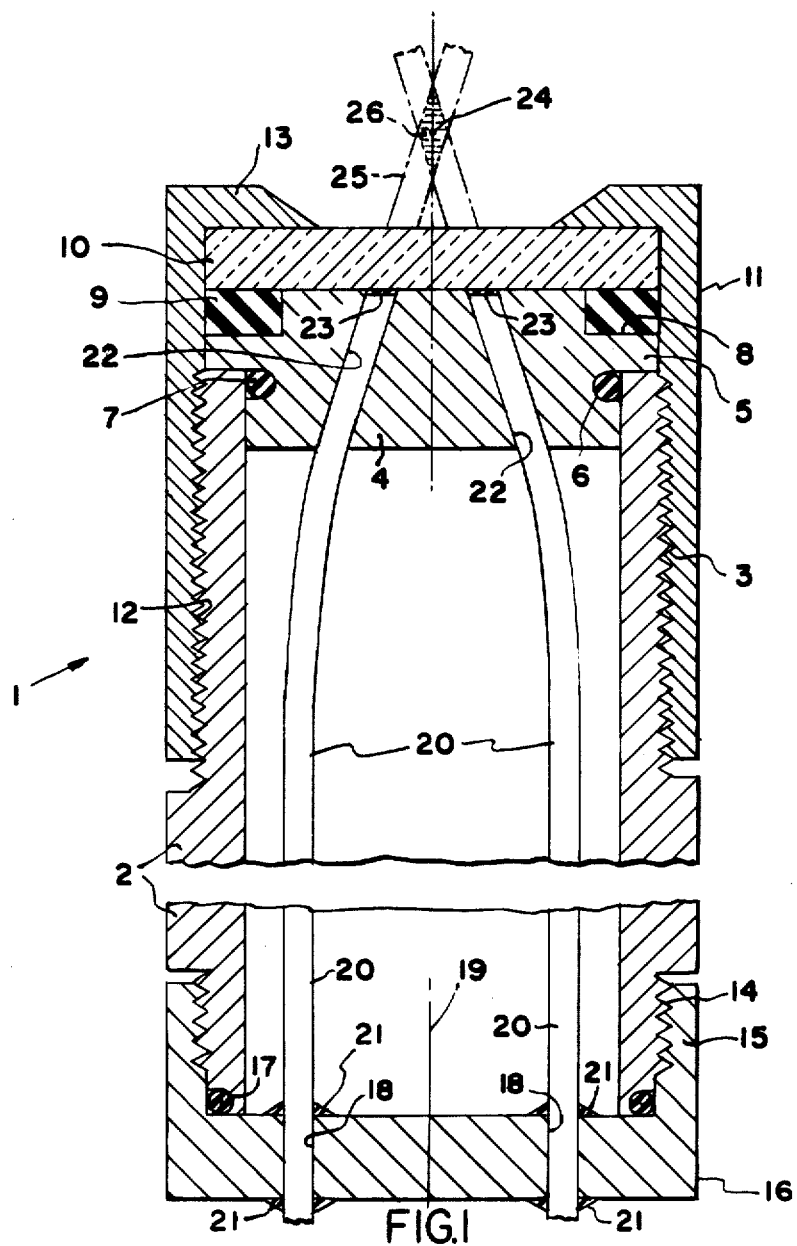

FIBER OPTIC PROBE

This invention relates to a fiber optic probe that is particularly useful for in-situ detection and measurement of the intensity of light scattered by particles suspended in a transparent or translucent fluid medium.

BACKGROUND OF THE INVENTION

In the practice of many chemical processes proper control of the process requires detection of the presence of a suspended phase in the reaction medium and determination of its concentration, particle size, or both. An example of such a process is one in which crystals are to be formed in a reaction liquid. Detection of the onset of crystallization usually is necessary to control the process in such manner as to yield crystals of the desired size and purity. Detection of the onset of crystallization currently is accomplished by visual monitoring of the reaction medium, detection of the exotherm resulting from the heat of crystallization, or detection of an increase of the turbidity of the reaction medium as a result of the presence therein of crystals. These known methods often lack sufficient sensitivity and dynamic range for proper process control.

SUMMARY OF THE INVENTION

A fiber optic probe constructed in accordance with the invention makes use of the phenomenon that light traversing a transparent or translucent fluid medium containing particles whose refractive index differs from that of the medium results in the scattering of some of the light. This effect is known as Tyndall scattering. The fraction of the light scattered per unit of light path length depends on the surface area of the particles, the refractive indices of the medium and the particles (or, if the particles are opaque, on the reflectivity of the particle surface), and upon the relative sizes of the particles with respect to the wavelength of the iluminating light. At relatively low particle concentrations, the scattered light fraction is substantially linear with the concentration, assuming the other factors to be relatively constant. At relatively high concentrations, however, both the illuminating light and the scattered light are attenuated by secondary scattering, resulting in non-linearity of the collected scattered light with concentration.

A probe according to the invention employs one or more optical fibers for transmitting light from a source to a continuous phase reaction medium so as to illuminate a predetermined area or zone thereof. The probe also employs one or more optical fibers to collect light scattered by particles in the illuminated zone and transmit such collected light to a detector. The use of optical fibers enables the illuminating light source and the collected light detector to be located at safe distances from the medium being monitored.

Both sets of fibers, i.e., the illuminating light fibers and the scattered light collecting fibers, are enclosed in a single fluid tight probe housing having a transparent window at one end which confronts the medium to be examined. The material from which the housing is made is one which can withstand the heat and constituency of the medium so as to be capable of immersion in the medium itself and at any desired area and depth thereof. The optical fibers are so oriented to the longitudinal axis of the probe housing that the longitudinal axes of the illuminating light fibers insect the longitudinal axes of the collected light fibers at a common point on the longitudinal axis of the housing. This arrangement provides an adequate zone of illumination and an adequate illuminated field of view.

THE DRAWINGS

Probes constructed in accordance with the invention are illustrated in the accompanying drawings, wherein:

FIG. 1 is a fragmentary sectional view of one embodiment and taken on the line 1—1 of FIG. 2;

FIG. 6 is a diagrammatic illustration of the manner in which a probe according to the invention may be used.

DETAILED DESCRIPTION

Figure 2:
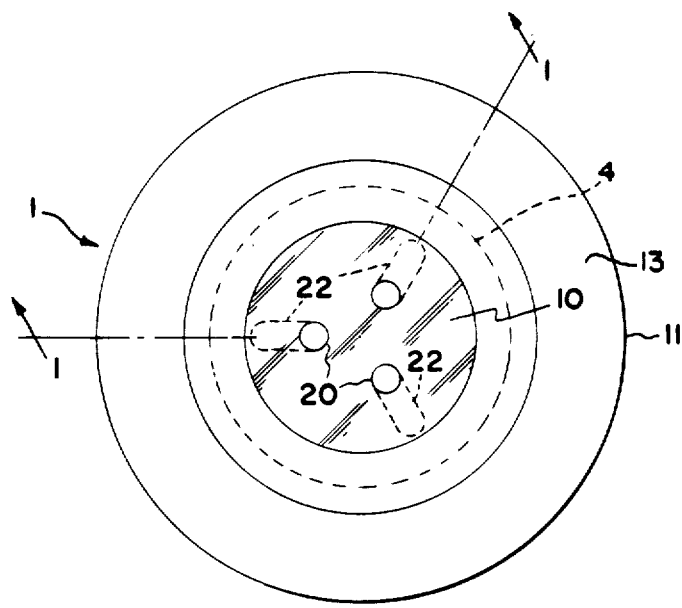
FIG. 2 is an end elevational view of the embodiment of FIG. 1.

A probe constructed in accordance with the embodiment of FIG. 1 is designated generally by the reference character 1 and comprises a hollow, cylindrical, elongate housing 2 formed of suitable metal or other material capable of immersion in a fluid medium that is to be monitored. Hereinafter the fluid medium sometimes will be referred to as the sample. The body 2 has external threads 3 at one end thereof. Fitted into the threaded end of the housing 2 is a support 4 having a flange 5 which seats on the free end of the housing. Adjacent the flange is a groove 6 in which is accommodated a sealing ring 7 so as to provide a fluid tight joint between the support and the interior of the housing. The support 4 also is provided with an annular groove 8 on which seats another seal 9.

Seated upon the support 4 and the annular seal 9 is a transparent window 10 of suitable thickness, such as 2 mm, and formed of a suitable material, such as glass, quartz, sapphire, and the like. The support 4 and the window 10 are maintained in assembled relation by means of a cap 11 having an internally threaded bore 12 in which the threaded end of the housing 2 is accommodated. The cap has a flange 13 which overlies and seats upon the marginal edge of the window 10.

The opposite end of the housing 2 is exteriorly threaded as at 14 for accommodation in a correspondingly threaded skirt 15 of a cap 16. A suitable seal 17 is interposed between the end of the housing 2 and the skirt 15.

The cap 16 is provided with three axially extending openings 18 which are radially and circumferentially spaced at uniform distances about the longitudinal axis 19 of the housing 2. The circumferential spacing between each opening 18 is 120°.

Extending through each of the openings 18 is an optical fiber 20 of preferably uniform diameter. Suitable seals 21 provide a fluid tight connection between the cap 16 and the fibers 20. The fibers extend through the housing and have corresponding ends fixed in openings 22 formed in the support 4. The openings 22 also are radially and circumferentially spaced uniformly about the axis 19 of the housing, but unlike the openings 18, the openings 22 converge in a direction toward the adjacent end of the housing. The angle of convergence may vary, as will be explained. All of the fibers 20 extend through the openings 22 and corresponding ends thereof abut the inner surface of the window 10. Preferably, a thin coating 23 of an optical coupling gel or oil having a refractive index similar to that of the fibers and the window is interposed between the window and the confronting ends of the fibers to reduce reflection losses at the fiber/window interface.

At least one of the fibers 20 has its free end located in a position to receive light from a source and transmit such light through the window 10 to illuminate a zone of a fluid sample. The remaining fibers may be coupled to one or more light detectors as will be explained in more detail hereinafter. For the time being, however, it is sufficient to state that the longitudinal axes of all of the fibers 20 intersect one another and the longitudinal axis 19 of the probe 1 at a common point 24 which lies on the longitudinal axis of the probe beyond the outer surface of the window 10. The diameter of the illuminating fiber is such that a substantially cylindrical beam 25 of light passes through the window into the sample. The diameter of the collected light fibers preferably corresponds to that of the illuminating fiber so that, where the extended axes of the fibers intersect, there is formed a field of view 26 having the configuration of two back-to-back cones. The significance of this will be explained hereinafter.

Figure 3:
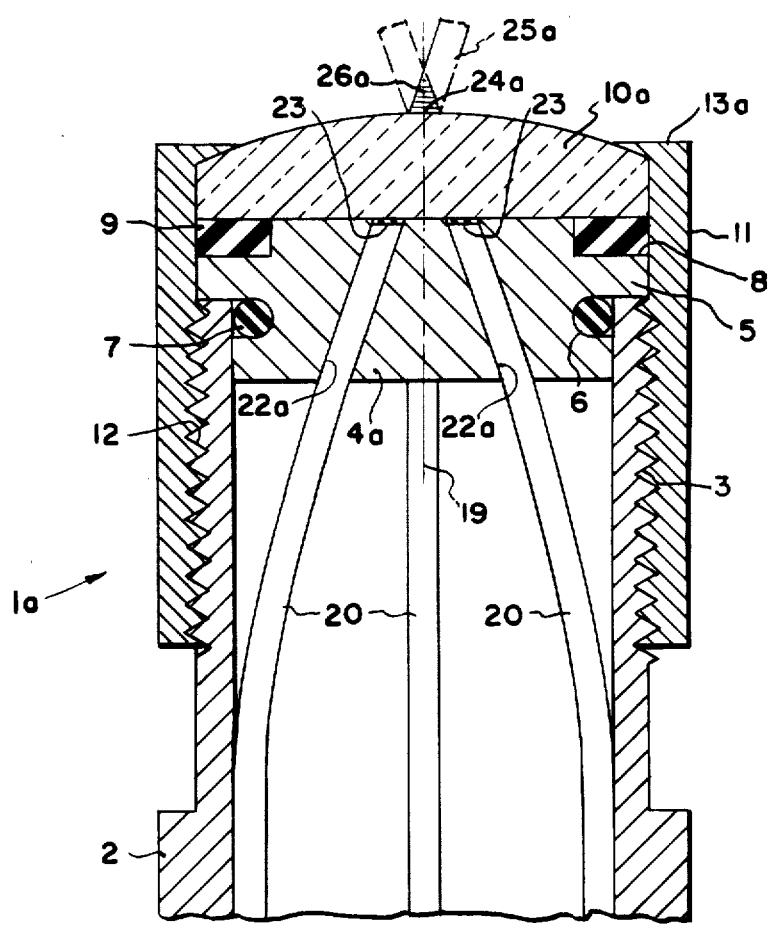
FIG. 3 is a view similar to FIG. 1, but taken on the line 3—3 of FIG. 4 and illustrating another embodiment.

FIG. 3 discloses a probe 1a which corresponds to the probe 1 except that the probe 1a has a window 10a having a convex outer surface and the flange 13a at the free end of the cap 11 is configured to accommodate and seat upon the concave surface. The greatest thickness of the window 10a is at the probe axis 19 and may be about 3 mm. Another difference between the probes 1 and 1a is that the support 4a of the latter has four openings 22a therein instead of three. The openings 22a are uniformly radially and circumferentially spaced about the longitudinal axis 19 of the probe 1a and the longitudinal axes of the fibers converge and intersect one another and the axis 19 at a common point 24a. The angle of convergence with respect to the axis 19 is about 20°. The intersection point 24a does not extend beyond the outer surface of the window 10a, but instead coincides therewith.

Accommodated in each of the openings 22a is one of the optical fibers 20. Two diametrically opposed fibers are coupled to one or more light sources for transmitting light beams 25a through the window 10a into the sample, whereas the other two fibers are associated with one or more light detectors for transmitting thereto light scattered by particles in that zone of the sample adjacent the point 24a.

As is apparent from FIG. 3, the field of view 26a resulting from the intersection of the fiber axes and the housing axis is substantially conical in configuration with the base of the cone coinciding with the outer surface of the window 10a. The field of view 26a, therefore, is less than the field of view 26.

Figure 5:
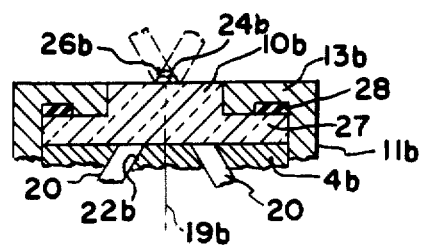
FIG. 5 is a view similar to FIG. 3, but illustrating a further embodiment.

It is not necessary to use a window having a convex external surface to obtain a conical field of view like that indicated at 26a. As is shown in FIG. 5, the window 10a may be replaced by a window 10b having a flat outer surface and a peripheral flange 27 which underlies a flange 13b at the free end of a cap 11b. Between the flanges 13b and 27 is an annular seal 28. A support 4b like the supports 4 and 4a underlies the inner surface of the window 10b and is provided with openings 22b for either three or four optical fibers 20 whose longitudinal axes converge and intersect one another and the probe axis 19 at a common point 24b located at the outer surface of the window 10b, as a consequence of which the field of view 26b is conical and has its base at the outer surface of the window.

In conditioning any of the disclosed probes for use, optical fibers which are to transmit light into the sample have those ends which are remote from the sample optically connected to a suitable light source 29. See FIG. 6. Such fiber or fibers hereinafter will be referred to as the illuminating fiber or fibers. The remote ends of the remaining fibers are connected to one or more suitable light detecting and intensity measuring devices 30 and 31, respectively. Such remaining fibers hereinafter will be referred to as the light collecting fibers. For convenience of illustration only one illuminating fiber and one light collecting fiber are shown in FIG. 6.

A suitable source of light is a light emitting diode (LED), a laser diode, a continuous wave (CW) gas laser, an incandescent lamp, and a spectral lamp. Suitable detectors 30 include photodiodes and photomultipliers. A suitable intensity measuring device 31 is a photometer. The preferred detection and measuring devices comprise a photodiode and a transimpedance amplifier the output from which is coupled to a suitable control computer 32 or the like which is operable to control the process.

If light other than that intentionally transmitted to the sample is present, an optical filter 33 can be interposed between the collecting fiber end and the detector so as to exclude from the latter light having wavelengths other than those emitted by the light source.

If a high degree of ambient light exclusion is required, the light source 29 may be a monochromatic CW gas laser, a laser diode, or a spectral lamp, and the filter 33 29 may be a narrow band pass filter or a monochromator.

In use, the probe 1 may be inserted via conventional tube fittings into a vessel 34 containing the sample 35 to be examined for the presence of particles or the probe may be immersed in the medium at any desired location within the latter.

Although the term "particles" is used herein, such term is intended to encompass all forms of materials present in discontinuous form in a reaction medium. Thus, the term "particles" is intended to apply to materials such as liquid droplets in a gas or in an immiscible liquid, gas bubbles in a liquid, or solid particulate in a gas or liquid.

The embodiment shown in FIG. 1 is preferred for use in the monitoring of samples containing low concentrations of particles. This is because a sample containing a low concentration is less turbid than one having a greater concentration, as a consequence of which there is less obstruction to penetration of the sample by the illuminating light beam. Thus, the beam 25 is capable of illuminating a relatively deep zone of the sample.

The field of view 26 is determined by projecting the diameter of the collected light fiber 20 beyond the outer surface of the window 10 so that it intersects the beam 25. Any particles in the field of view will reflect or scatter some of the light and some of the scattered light will be collected by the collected light fiber and be transmitted by the latter to the detector and intensity measuring devices.

Figure 4:
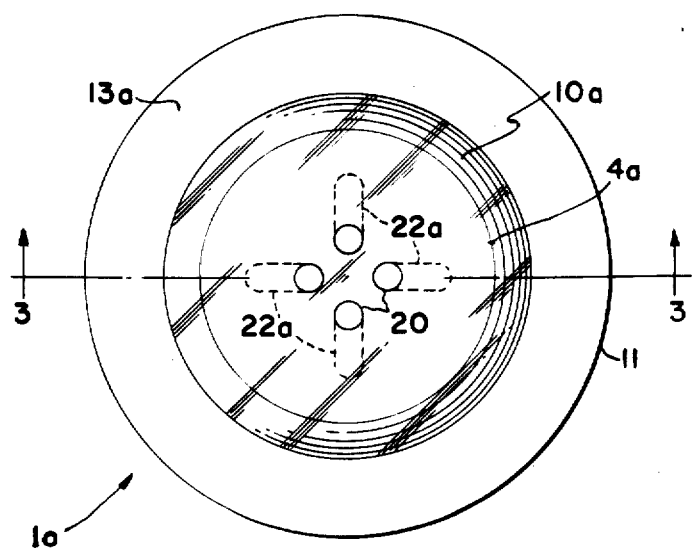
FIG. 4 is an end elevational view of the embodiment of FIG. 3.

In those instances in which the concentration of particles in the sample is relatively high, the probe 1 of FIG. 3 or 4 is preferred. In such case the light beams 25a emitted by the illuminating fibers have a relatively shallow penetration into the sample, but the field of view 26a commences at the exterior surface of the window, thereby enabling light scattered by particles in the field of view to be collected by the collected light fibers.

The sensitivity of probes constructed according to the invention is dependent upon (1) the amount of light conducted to the field of view, (2) the efficiency with which the light scattered by the particles in the sample is collected and transmitted to the detector, and (3) the efficiency with which light other than that scattered by the particles (extraneous light) is excluded.

For detection of very small concentrations of particles (in the parts per million to parts per billion range) exclusion of extraneous light is the most important consideration. A major source of extraneous light results from reflection of the illuminating light at the interface between the sample and the window. Typically $10^{-5}$ to $10^{-2}$ Watts (W) of light are used to illuminate the sample. The reflection at the window sample interface is typically about 0.1 to 1%, or $10^{-4}$ to $10^{-8}$ W, and varies with the refractive index of the sample. The scattered light collected from very low concentrations of particles may be as low as $10^{-13}$ W. Accordingly it is necessary to exclude virtually all of the reflected light.

The geometry of the probes disclosed herein has been selected to yield maximum exclusion of reflected light consistent with otherwise acceptable performance. This is accomplished by choosing the angle between the fiber axes and the probe axis, the radial spacing of the fibers from such axis, the circumferential spacing between the fibers, and the window thickness so that reflection from the window does not fall on any of the collecting fiber ends. Typically, these factors are so selected that such reflected light falls either on the probe axis or on that side of the probe axis opposite the illuminating fiber and between adjacent collecting fibers. By positioning illuminating fibers diametrically opposite one another, light reflected from one such fiber cannot fall on a light collecting fiber.

The amount of light collected and transmitted by the collecting fibers is approximately proportional to (1) their total cross sectional area (i.e., the product of the number of collecting fibers and the cross-sectional area of each), (2) the square of the distance between the ends of the fibers and the intersection of their axes, and (3) the angle between the illuminating fiber(s) and the collecting fiber(s). The optimum angle was found experimentally to be between about 20° to 25° for particles with diameters between 0.2 and 200 microns, but angles between about 10° and 30° yielded sensitivities within about 30% of the maximum.

A radial distance from the fiber to the probe axis of two to three times the fiber core diameter was found to yield satisfactory results for three and four fiber probes in which the angle between the fiber axes and the probe axis is between 10° and 25°. The choice of the circumferential spacing between the illuminating fibers and the collecting fibers also represents a compromise between sensitivity and extraneous light reflection, with relatively small spacing (less than 90°) yielding better extraneous light rejection, but poorer sensitivity than larger spacing (over 90°). In practice, circumferential spacing of between 60° and 120° performs well.

Assuming that the circumferential spacing between the fibers and the ratio between the fiber diameter and the distance to the probe axis are constant, the sensitivity is approximately proportional to the fiber core diameter. This results from the fact that both the cross sectional area of the fibers and the square of the distance to the intersection are proportional to the square of the fiber diameter, while the depth of field (i.e., the length of the region in which the fields of view of the illuminating fibers and the collecting fibers overlap) increases with the fiber diameter. Plastic clad silica fibers having a core diameter of from about 200 to 600 microns are most suitable. The larger diameters (about 600 microns) perform slightly better and are easiest to handle and are thus preferred. Fibers with larger core diameters are more expensive and require probes of large diameter, due to their large bending radii, and are thus less desirable.

The diameter of the illuminating fibers may be identical to each other and to that of the collecting fibers. When used in conjunction with LEDs or extended light sources, such as incandescent lamps or spectral lamps, smaller fibers will generally transmit less light to the sample and larger fibers increase the extraneous light more than they increase the illumination of the region viewed by the collection fibers. When focused beams from CW lasers or laser diodes are used for illumination, fibers with core diameters smaller than those of the collection fibers are preferred because their use results in less extraneous light due to the smaller diameter of the reflection from the window sample interface. Further, the depth of field of the probe is reduced, due to the smaller diameter of the illuminating beam, which results in increased dynamic range. Illuminating fibers with core diameters of 100 to 300 microns perform well in conjunction with laser light sources and 600 micron diameter collecting fibers.

The number of collecting fibers employed represents a compromise between sensitivity and expense. One collecting fiber is sufficient for most applications, but more are advantageous for applications requiring high sensitivity.

One illuminating fiber is sufficient to collect the light from a light emitting diode, laser, or laser diode, whereas two or more are advantageous for collecting light from extended sources.

Probes with more than the minimum number of fibers required for the measurement provide redundancy which is advantageous in case of fiber breakage.

The disclosed embodiments are representative of presently preferred embodiments of the invention, but are intended to be illustrative rather definitive thereof. The invention is defined in the claims.

What is claimed is:

1. A fiber optic probe comprising a housing having a longitudinal axis; a transparent window closing one end of said housing and having inner and outer surfaces; and a plurality of elongate optical fibers within said housing and constituting all of the optical fibers within said housing, all of said fibers having their corresponding ends terminating adjacent and confronting the inner surface of said window and extending in a direction away from said window through and outwardly of said housing, said corresponding ends of all of said fibers being radially spaced from the axis to said housing and circumferentially spaced from one another, said corresponding ends of all of said fibers having their longtitudinal axes converging toward one another in a direction toward the outer surface of said window and intersecting one another at a common point on the axis of said housing.

2. A probe according to claim 1 wherein said common point is substantially at said outer surface.

3. A probe according to claim 1 wherein said common point is spaced beyond said outer surface.

4. A probe according to claim 1 wherein said window has a flat outer surface.

5. A probe according to claim 1 wherein said window has a convex outer surface.

6. A probe according to claim 1 wherein the radial spacing from the axis of said housing to the longitudinal axis of each of said fibers at said corresponding end thereof is substantially uniform.

7. A probe according to claim 1 wherein the circumferential spacing between the axes of said fibers at the corresponding ends thereof is substantially uniform.

8. A probe according to claim 1 wherein the radial spacing from the axis of said housing to the longtudinal axis of each of said fibers at said corresponding end thereof is substantially uniform and wherein the circumferential spacing between the axes of said fibers at the corresponding ends thereof is substantially uniform.

9. A probe according to claim 8 wherein there are at least three of said fibers.

10. A probe according to claim 8 wherein there are at least four of said fibers.

11. A probe according to claim 1 including an optical coupling fluid interposed between said window and the confronting ends of said fibers.

12. A probe according to claim 1 wherein said common point is spaced from the outer surface of said window a distance sufficient that imaginary extensions of said fibers intersect one another and form externally of said window a pair of back-to-back conical zones lying along the axis of said housing and on opposite sides of said point.

13. A probe according to claim 1 wherein said common point is so located with reference to the outer surface of said window that imaginary extensions of said fibers intersect one another and form externally of said window a single conical zone extending along the axis of said housing.

14. A probe according to claim 1 wherein said window is formed from a material selected from the class consisting of glass, quartz, and sapphire.

15. A probe according to claim 1 wherein the corresponding ends of all of said fibers abut said window.

16. A fiber optic probe comprising a cylindrical housing closed at one end by a transparent window having an outer surface adapted to interface a fluid sample and at its opposite end by a wall; a plurality of optical fibers extending into said housing and having corresponding ends confronting said window; support means positioning said fibers with their longitudinal axes uniformly spaced radially from the axis of said housing, said confronting ends of said fibers converging in the direction of said window along lines which intersect at a common point on the longitudinal axis of said housing; a source of light coupled to at least one of said fibers for transmission thereby through said window to illuminate a zone adjacent said common point, the presence of particles in said illuminated zone enabling light to be reflected through said window and collected by the remaining fibers for transmission thereby outwardly of said housing; and means for detecting light transmitted by said remaining fibers.

17. A probe according to claim 16 wherein said common point is spaced beyond the outer surface of said window.

18. A probe according to claim 16 wherein said common point substantially coincides with the outer surface of said window.

19. A probe according to claim 16 wherein the longitudinal axes of said fibers at said corresponding ends are substantially uniformly circumferentially spaced from one another.

20. A probe according to claim 16 wherein the circumferential spacing between adjacent fibers at said corresponding ends is such that no reflection of light from said interface falls on any of said remaining fibers.

21. A probe according to claim 16 wherein said source of light is coupled to a number of said fibers, each of said number of fibers being diametrically opposed to another of such fibers.

22. A probe according to claim 21 wherein the corresponding ends of all of said fibers abut said window.

23. A probe according to claim 1 wherein each of said fibers is circular in cross-section and wherein the spacing between the axis of said probe and the longitudinal axis of each of said fibers at the corresponding end thereof is greater than the diameter of such fiber.

24. A fiber optic probe comprising a housing having a longitudinal axis; a transparent window closing one end of said housing and having inner and outer surfaces; and a plurality of elongate, cylindrical, substantially uniform diameter optical fibers all of which have their corresponding ends within said housing and abutting said window, said corresponding ends of all of said fibers being radially spaced from the axis of said housing and circumferentially spaced from one another, said corresponding ends of all of said fibers having their longitudinal axes converging toward one another at such an angle that they intersect one another at a common point on the axis of said housing externally of said window, the angle of convergence between the fiber axes and the probe axis, the circumferential spacing between the corresponding ends of said fibers, the radial spacing between the axes of said fibers and the axis of said housing, and the thickness of said window being so selected that light transmitted via any one of said fibers in a direction toward said window may not be reflected from said window onto the corresponding end of another of said fibers.

* * * * *

UNITED STATES PATENT AND TRADEMARK OFFICE
CERTIFICATE OF CORRECTION

PATENT NO. : 4,707,134

DATED : Nov. 17, 1987

INVENTOR(S) : Richard D. McLachlan; Leslie D. Rothman

It is certified that error appears in the above-identified patent and that said Letters Patent is hereby corrected as shown below:

Col. 5, line 44, after "(2) the" insert --inverse of the--.

Col. 6, line 60, delete "to" and insert --of--.

Col. 8, Claim 23, line 29, delete "circular" and insert --cylindrical--.

Signed and Sealed this

Fourteenth Day of June, 1988

Attest:

DONALD J. QUIGG

*Attesting Officer*   *Commissioner of Patents and Trademarks*